United States Patent
Shin et al.

(10) Patent No.: US 7,723,562 B2
(45) Date of Patent: May 25, 2010

(54) MICE LACKING ALPHA 1G SHOWING ENHANCED NOVELTY-SEEKING AND ALCOHOL PREFERENCE AND THERAPEUTIC METHODS FOR MOOD DISORDERS BY MODULATING ALPHA 1G T-TYPE CALCIUM CHANNELS

(75) Inventors: Hee-Sup Shin, Seoul (KR); Daesoo Kim, Seoul (KR); Jungryun Lee, Seoul (KR); Soonwook Choi, Seoul (KR); Chanki Kim, Seoul (KR); Sukchan Lee, Seoul (KR)

(73) Assignee: Korea Institute of Science and Technology (KR)

( * ) Notice: Subject to any disclaimer, the term of this patent is extended or adjusted under 35 U.S.C. 154(b) by 0 days.

(21) Appl. No.: 12/351,316

(22) Filed: Jan. 9, 2009

(65) Prior Publication Data

US 2009/0126031 A1    May 14, 2009

Related U.S. Application Data

(63) Continuation-in-part of application No. 10/971,976, filed on Oct. 22, 2004, now abandoned.

(30) Foreign Application Priority Data

May 4, 2004 (KR) .................. 10-2004-0031406
May 17, 2004 (KR) .................. 10-2004-0034744

(51) Int. Cl.
*A01K 67/00* (2006.01)
*A01K 67/033* (2006.01)
*A01K 67/027* (2006.01)
*G01N 33/00* (2006.01)

(52) U.S. Cl. .............................. 800/3; 800/13; 800/14; 800/18

(58) Field of Classification Search ............ None
See application file for complete search history.

(56) References Cited

OTHER PUBLICATIONS

Cloninger, "A Unified Biosocial Theory of Personality and its Role in the Development of Anxiety States," *Psychiatric Dev.* 3:167-226 (1986).

Kim et al., "Thalamic Control of Visceral Nociception Mediated by T-Type $Ca^{2+}$ Channels," *Science* 302:117-119 (2003).

Kim et al., "Lack of the Burst Firing of Thalamocortical Relay Neurons and Resistance to Absence Seizures in Mice Lacking $\alpha_{1G}$ T-Type $Ca^{2+}$ Channels," *Neuron* 31:35-45 (2001).

Perez-Reyes, "Molecular Physiology of Low-Voltage-Activated T-Type Calcium Channels," *Physiol. Rev.* 83:117-161 (2003).

Tsien, "Calcium Channels In Excitable Cell Membranes", *Annu. Rev. Physiol.* 45:341-358 (1983).

*Primary Examiner*—Anne-Marie Falk
(74) *Attorney, Agent, or Firm*—Klarquist Sparkman, LLP

(57) ABSTRACT

The present invention relates to a novel use of an α1G T-type calcium channel transgenic mouse as a nervous disease model, more particularly, a novel use of a mouse deficient in α1G T-type calcium channel showing novelty-seeking and alcohol preference as a nervous disease model for human nervous related diseases such as novelty-seeking character, alcoholism, anxiety and emotion disorder by stress, etc. The α1G T-type channel transgenic mice showing novelty-seeking and alcohol preference of the present invention can be effectively used for the development of a medicine and a therapeutic method for human nervous diseases.

13 Claims, 11 Drawing Sheets

MICE LACKING ALPHA 1G SHOWING ENHANCED NOVELTY-SEEKING AND ALCOHOL PREFERENCE AND THERAPEUTIC METHODS FOR MOOD DISORDERS BY MODULATING ALPHA 1G T-TYPE CALCIUM CHANNELS

CROSS REFERENCE TO RELATED APPLICATIONS

This is a continuation-in-part application of U.S. patent application Ser. No. 10/971,976, filed on Oct. 22, 2004 now abandoned, which in turn claims the benefit of Korean Application No. 10-2004-0031406, filed on May 4, 2004 and Korean Application No. 10-2004-0034744 filed on May 17, 2004.

FIELD OF THE INVENTION

The present invention relates to a novel use of an α1G T-type calcium channel transgenic mouse as a nervous disease model, more particularly, a novel use of a mouse deficient in α1G T-type calcium channel showing novelty-seeking and alcohol preference as a nervous disease model for human nervous related diseases such as novelty-seeking character, alcoholism, anxiety and emotion disorder by stress, etc.

BACKGROUND

A man of novelty-seeking character has greater preference to a new subject or a medicine that is untouched yet. So, he is apt to show strange or dangerous behavior such as an adventure or a crime and be an alcoholic or a compulsory shopper with ease. However, physiological or genetic mechanisms involved in such behavior have not been discovered, yet.

A strange subject or a new environment not only causes curiosity but also anxiety or fear of its potential danger (Bronson, G. W., *Psychol. Bull.* 69, 350-358, 1968; Marks, I., *J. Child Psychol. Psychiatry* 28, 667-697, 1987). According to TPQ (Tri-dimensional Character Questionnaires) classification by Dr. Cloninger, people having a novelty-seeking character feel anxiety or fear of a strange subject less than others (Cloninger, C. R., *Psychiatr. Dev.* 4, 167-226, 1986). They enjoy adventures, dislike fixed idea, and have interests on various subjects of in variety of fields (Cloninger, C. R., *Psychiatr. Dev.* 4, 167-226, 1986; Cloninger, C. R. et al., *Psychol. Rep.* 69, 1047-1057, 1991; Maggini, C. et al., *Compr. Psychiatry* 41, 426-431, 2000). Dr. Noble at UCLA reported in 1998 that certain alleles of dopamine receptors DRD2 and DRD4 were found in people who were especially fond of alcohol, tobacco, drugs and adventurous behavior such as sky diving, bungee jump, etc (Noble, E. P. et al., *Am. J. Med. Genet.* 81, 257-267, 1998). However, a mechanism of human brain related to preference to such dangerous or strange stimuli has still been in question. That is because a proper animal model for studies on novelty-seeking character has not been given and no target molecule but a dopamine receptor has been found.

Voltage-dependent calcium channels are involved in increasing intracellular calcium content by the activation of neurons (Tsien, R. W., *Annu. Rev. Physiol.* 45, 341-358, 1983), and are classified into high-voltage dependent channels and low-voltage dependent channels (Tsien, R. W. et al., *Trends Neurosci.* 18, 52-54, 1995). T-type calcium channel is a representative low-voltage dependent channel and has three subclasses of Cav3.1(α1G), 3.2(α1H) and 3.3(α1I) according to the genotype for α1 subunit (Perez-Reyes, E., *Physiol. Rev.* 83, 117-161, 2003). α1G calcium channel is involved in the production of burst firings of neurons in thalamus and its relevant pathological functions have just recently been disclosed (Kim, D. et al., *Science* 302, 117-119, 2003; Kim, D. et al., *Neuron* 31, 35-45, 2001).

According to the studies on mice deficient in α1G calcium channel along with other pharmacological reports, α1G calcium channel is involved in the generation of SWDs (spike-and-wave discharge) of absence epilepsy by receiving signals from GABAB receptor (Kim, D. et al., *Neuron* 31, 35-45, 2001), and the suppression of continuous pain signal during the transmission of sensory signal, which is a major function of thalamus (Kim, D. et al., *Science* 302, 117-119, 2003). However, the effect of lacking in α1G T-type calcium channel on the behavior of an individual has not been explained.

Thus, the present inventors have observed mice deficient in α1G T-type calcium channel in the aspects of behavioral science. As a result, the present inventors have discovered that α1G transgenic mice have novelty-seeking and alcohol preference, and have completed this invention by confirming that those transgenic mice can be effectively used for the development of a medicine and a therapeutic method for human nervous diseases by using the mice as a nervous disease model for human nervous diseases such as novelty-seeking character, alcoholism, emotion disorder by stress and irregularity of desire, etc.

SUMMARY OF THE INVENTION

It is an object of this invention to provide a use of mice deficient in α1G T-type calcium channel as a nervous disease model for human nervous diseases including novelty-seeking character, alcoholism, emotion disorder by stress and irregularity of desire, etc.

DETAILED DESCRIPTION OF PREFERRED EMBODIMENTS

In order to achieve the above object, the present invention provides a use of mice deficient in α1G T-type calcium channel as a nervous disease model for human nervous diseases including novelty-seeking character and alcoholism, etc.

In one embodiment, the present invention provides a method of identifying a compound with potential for treatment of novelty-seeking character or alcoholism comprising:

a) administering one or more test compounds to α1G T-type calcium channel knockout mice having α1G–/– genotype, wherein the mice are an animal model of novelty-seeking character or alcoholism; and b) determining whether the test compound inhibits at least one behavioral aspect of said mice related to novelty-seeking character or alcoholism; wherein inhibition of the behavioral aspect is indicative of a compound with potential for treatment of novelty-seeking character or alcoholism. In some examples, the test compound inhibits the behavioral aspect related to novelty-seeking character or alcoholism as compared to a control. The control can be a mouse (such as a α1G+/+ mouse or a α1G+/– mouse) that is administered the same one or more test compounds as the α1G–/– mouse or the control can be a mouse (such as a wild type mouse, a α1G+/– mouse, or a α1G–/– mouse) that has not been administered the one or more test compounds (such as a mouse that has been treated with vehicle alone, or untreated). In a particular example, the control is a α1G–/– mouse that has not been administered the one or more test compounds (such as a α1G–/– mouse that has been treated with vehicle alone, or an untreated mouse).

In particular examples, the behavioral aspect is reactivity to a new environment, reactivity to a new subject, or alcohol preference. In some examples, reactivity to a new environment includes mobility, activity, or locomotion of the mouse when it is placed in a new environment (for example, a new cage or an open field environment). Inhibition of reactivity to a new environment includes a decrease (such as at least 10%, at least 20%, at least 30%, at least 50%, at least 70%, at least 80%, at least 90%, or at least 95% decrease) in activity (such as distance traveled in a set period of time, number of beam crossings in an photocell open field cage, or time spent in the center of the open field) as compared to a control.

In further examples, reactivity to a new subject (such as a new object or material placed in the animal's environment) includes approaching the new subject, contact with the new subject (such as latency to first contact or number or duration of contacts), and play behavior with the new subject (including pushing, towing, or biting the new subject, or digging around the new subject). Inhibition of reactivity to a new subject includes a decrease (such as at least 10%, at least 20%, at least 30%, at least 50%, at least 70%, at least 80%, at least 90%, or at least 95% decrease) in approach, number or duration of contact, or play behavior with the new subject as compared to a control. Inhibition of reactivity to a new subject includes an increase (such as at least 10%, at least 20%, at least 30%, at least 50%, at least 70%, at least 80%, at least 90%, or at least 95% increase) in latency to first contact with the new subject as compared to a control.

In still further examples, alcohol preference includes increased consumption of an alcohol solution (such as 8% alcohol) as compared to water in a two bottle choice test. Inhibition of alcohol preference includes a decrease (such as at least 10%, at least 20%, at least 30%, at least 50%, at least 70%, at least 80%, at least 90%, or at least 95% decrease) in alcohol consumption (such as percent of total consumption, or volume consumed) as compared to a control.

In some examples, the α1G T-type calcium channel knockout mice show increased searching mobility when a new environment is given or increased reactivity to a new subject, compared to wild-type mice.

In another embodiment, the present invention provides a method of identifying a candidate compound for treatment of novelty-seeking character comprising:

a) administering one or more test compounds to α1G T-type calcium channel knockout mice having α1G−/− genotype, wherein the mice are an animal model of novelty-seeking character; and b) determining whether the test compound inhibits searching action for a new material or play behavior with the new material, wherein inhibition of the searching action or the play behavior is indicative of a compound with potential for treatment of novelty-seeking character. In some examples, the test compound inhibits the searching action or the play behavior as compared to a control. The control can be a mouse (such as a α1G+/+ mouse or a α1G+/− mouse) that is administered the same one or more test compounds as the α1G−/− mouse or the control can be a mouse (such as a wild type mouse, a α1G+/− mouse, or a α1G−/− mouse) that has not been administered the one or more test compounds (such as a α1G−/− mouse that has been treated with vehicle alone, or untreated). In a particular example, the control is a α1G−/− mouse that has not been administered the one or more test compounds (such as a mouse that has been treated with vehicle alone, or an untreated mouse).

In particular examples, searching actions for a new material includes approach or contact with the new material. Inhibition of searching action includes a decrease (such as at least 10%, at least 20%, at least 30%, at least 50%, at least 70%, at least 80%, at least 90%, or at least 95% decrease) in searching action for the new material as compared to a control. In additional particular examples, play behavior with the new material includes pushing, towing, or biting the new material, or digging around the new material. Inhibition of play behavior includes a decrease (such as at least 10%, at least 20%, at least 30%, at least 50%, at least 70%, at least 80%, at least 90%, or at least 95% decrease) in play behavior with the new material as compared to a control. In some examples, the α1G T-type calcium channel knockout mice show increased searching action for a new material or play behavior with the new material as compared to wild type mice.

The present invention further provides a method of identifying a therapeutic agent for treating alcoholism comprising:

a) administering one or more test compounds to α1G T-type calcium channel knockout mice having α1G−/− genotype, wherein the mice are an animal model of alcoholism; and b) determining whether the test compound inhibits alcohol preference, wherein inhibition of the alcohol preference is indicative of a compound with potential for treatment of alcoholism. In particular examples, the test compound inhibits the alcohol preference as compared to a control. The control can be a mouse (such as a α1G+/+ mouse or a α1G+/− mouse) that is administered the same one or more test compounds as the α1G−/− mouse or the control can be a mouse (such as a wild type mouse, a α1G+/− mouse, or a α1G−/− mouse) that has not been administered the one or more test compounds (such as a mouse that has been treated with vehicle alone, or untreated). In a particular example, the control is a α1G−/− mouse that has not been administered the one or more test compounds (such as a α1G−/− mouse that has been treated with vehicle alone, or an untreated mouse). Inhibition of alcohol preference includes a decrease (such as at least 10%, at least 20%, at least 30%, at least 50%, at least 70%, at least 80%, at least 90%, or at least 95% decrease) in alcohol consumption (such as percent of total consumption, or volume consumed) as compared to a control.

In some examples, the α1G T-type calcium channel knockout mice show increased alcohol preference, compared to wild-type mice.

Hereinafter, the present invention is described in detail.

The present invention provides a method of identifying a compound with potential for treatment of novelty-seeking character or alcoholism comprising:

a) administering one or more test compounds to α1G T-type calcium channel knockout mice having α1G−/− genotype, wherein the mice are an animal model of novelty-seeking character or alcoholism; and b) determining whether the test compound inhibits at least one behavioral aspect of said mice related to novelty-seeking character or alcoholism; wherein inhibition of the behavioral aspect is indicative of a compound with potential for treatment of novelty-seeking character or alcoholism.

In order to investigate behavioral changes by lacking of α1G calcium channel of T-type calcium ion channels, α1G transgenic mice harboring a gene coding α1G protein devoid of its N-terminal region were used. The α1G transgenic mice were prepared by the method reported in "TRANSGENIC MOUSE WITH DISRUPTED CALCIUM ION CHANNEL ALPHA 1D GENE AND PRODUCTION METHOD THEREOF" (Korea Application No: 10-2001-0028803) applied for a patent by the present inventors on May 25, 2001.

Particularly, α1G transgenic mice were generated by gene targeting method. Gene targeting is a study method to determine the original function of a destroyed gene by observing pathological phenomena of an object harboring the destroyed gene after disrupting a certain gene in genome by introducing a targeting vector into the gene. The targeting vector of the present invention includes a homologous fragment of gene coding N'-deleted α1G protein, PGK-neo cassette, and thymidine kinase gene cassette located at 3'-end. Since homologous recombination takes place at the homologous fragment and N'-end of α1G protein is deleted thereby, wild-type α1G gene of the calcium channel is not expressed by the above targeting vector. In the preferred embodiments of the present invention, the present inventors generated a chimera mouse by inserting the cultured embryonic stem cell clone having targeted α1G gene into blastocoel of the blastula. After mating a female mouse having embryonic stem cell-inserted blastula with a male mouse having undergone vasectomy, transplantation was performed into a uterus of a 2.5 p.c. surrogate mother mouse. The surrogate mother mouse was raised for nineteen days, from which a chimera mouse having α1G+/− genotype was obtained. Finally, the present inventors generated a homozygote transgenic mouse having α1G−/− genotype by mating a male and a female mouse selected from the above mice having α1G+/− genotype.

The transgenic mice above were born normal, had equal life spans to normal mice, and both male and female were fertile when bred with wild-type mice.

The present inventors observed behaviors and studied on nervous disease related mechanisms of transgenic mice in which α1G T-type calcium channels are inhibited by lacking in some of α1G gene coding pore-forming subunit of T-type calcium ion channels.

At first, the present inventors observed behavioral changes of α1G−/− transgenic mice according to environmental changes. While investigating a new environment given, α1G−/− transgenic mice showed much increased mobility, compared to wild type mice (see FIGS. 1 and 2). In order to verify that, a new material was put in a breeding cage to which mice have already adapted. Then, reactivity was investigated. As a result, approach time to a new material was shorter but contact time was longer than wild type mice. In behavioral aspect, the transgenic mice dug around a new material and pushed, pulled or dragged the material, which were characteristic behaviors of those transgenic mice not observed in wild type mice (see FIG. 3).

The difference between α1G−/− transgenic mice and wild type mice in behavioral aspects resulted not from their different visual power to sense a new material but from their different brain reactivity to the new material (see FIG. 4).

The previously reported disease models showing increased mobility similar to that of α1G−/− transgenic mice are attention-deficit hyperactive disorder (Jaber, M. et al., C R Seances Soc Biol Fil 192, 1127-1137, 1998), schizophrenia (Mailman, R. B. et al., Appl Res Ment Retard 2, 1-12, 1981) and stereotype (Aman, M. G., J Autism Dev Disord 12, 385-398, 1982). Those diseases are equally characterized by high-grade recognition disorder including space learning.

In order to confirm whether or not predisposition of those diseases is related to increased mobility of α1G−/− transgenic mice, the present inventors investigated their learning capabilities. As a result, there was no significant difference between the transgenic mice and wild type mice in learning ability (see FIGS. 5, 6 and 7). According to previous reports, when increased mobility caused by a newly provided environment, like the case of α1G−/− transgenic mice, is not decreased after adaptation to a new environment, it leads to learning disability, suggesting difficulties in adaptation to a new surrounding. And the increase of pro-material or pro-environmental mobility shown by α1G−/− transgenic mice is not like the cases reported earlier.

This result is supported by other pharmacological test results. Amphetamine generally increases mobility but mitigates the increase of mobility when it is administered to a patient having attention-deficit hyperactive disorder, so that it has been used as a therapeutic agent for attention-deficit hyperactive disorder (Cirulli, F. and Laviola, G., Neurosci Biobehav Rev 24, 73-84, 2000). However, when amphetamine was administered to α1G−/− transgenic mice, active increase of mobility in early stage did not decrease and environment non-dependent mobility increased excessively (see FIG. 8). Lithium (Nolen, W. A., Ned Tijdschr Geneeskd 143, 1299-1305, 1999), an excitement inhibitor, which has been used as a therapeutic agent for manic-depression, was also proved not to affect mobility (see FIG. 9). Therefore, the reason for the mobility increase in α1G−/− transgenic mice is unknown even after pharmacological researches. Just when α1G−/− transgenic mice were pre-treated with lithium, searching actions for a new material were not much different but play behavior, generally increases after searching, was inhibited, indicating that excessive play behavior of a transgenic mouse is related to emotional changes in brain.

As explained hereinbefore, preference and increasing reactivity to a new material of a transgenic mouse are very similar to those of a man having sensation/novelty-seeking character. A man of sensation/novelty-seeking character prefers a new environment or new stimuli, so that he enjoys an adventure or even a dangerous action and is apt to be drug abuse but is less sensitive to stress or fear which is caused by a new environment or a stimulus than a normal person (Cloninger, C. R., Psychiatr Dev 4, 167-226, 1986; Cloninger, C. R. et al., Res Publ Assoc Res Nerv Ment Dis 60, 145-166, 1983; Maggini, C. et al., Compr Psychiatry 41, 426-431, 2000). α1G−/− transgenic mice of the present invention, like people having a novelty-seeking personalities, are less sensitive to environmental stress or stimulus inducing depression (see FIGS. 10 and 11).

Further, the present invention provides a method of identifying a compound with potential for treatment of novelty-seeking character or alcoholism comprising:

a) administering one or more test compounds to α1G T-type calcium channel knockout mice having α1G−/− genotype, wherein the mice are an animal model of novelty-seeking character or alcoholism; and b) determining whether the test compound inhibits at least one behavioral aspect of said mice related to novelty-seeking character or alcoholism; wherein inhibition of the behavioral aspect is indicative of a compound with potential for treatment of novelty-seeking character or alcoholism.

Alcohol preference of α1G−/− transgenic mice was significantly increased, compared to wild type mice (see FIG. 12), which was also similar to alcohol preference of people having a novelty-seeking character.

In conclusion, α1G−/− transgenic mice of the present invention are highly sensitive to pleasant feeling induced by a new environment, a strange subject or drugs including alcohol, but feel less stress. So, α1G−/− transgenic mice show very similar characteristics to a man of novelty-seeking character, making them a useful candidate for an animal model to test positive or negative effects of such characteristics.

Test Compounds

The methods disclosed herein are of use for identifying compounds that can be used to treat novelty-seeking behavior or alcoholism, such as compounds that inhibit novelty-seeking behaviors (for example, reactivity to a new environment or a new subject) or alcohol preference.

A "compound" is any substance or any combination of substances that is useful for achieving an end or result. The compounds identified using the methods disclosed herein can be used to modulate (for example, increase or decrease) novelty-seeking behaviors (for example, reactivity to a new environment or a new subject) or alcohol preference. Any compound that has potential (whether or not ultimately realized) to alter these behaviors can be tested using the methods of this disclosure.

Exemplary test compounds that can be screened for their ability to modulate novelty-seeking character and/or alcoholism or alcohol preference include, but are not limited to, peptides such as, for example, soluble peptides, including but not limited to members of random peptide libraries (see, e.g., Lam et al., *Nature,* 354:82-84, 1991; Houghten et al., *Nature,* 354:84-86, 1991), and combinatorial chemistry-derived molecular libraries made of D- and/or L-configuration amino acids, phosphopeptides (including, but not limited to, members of random or partially degenerate, directed phosphopeptide libraries; see, e.g., Songyang et al., *Cell,* 72:767-778, 1993), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), small organic or inorganic molecules (such as, so-called natural products or members of chemical combinatorial libraries), molecular complexes (such as protein complexes), or nucleic acids (e.g., siRNAs). In some examples, the compound is membrane permeable.

Sources of test compounds that can be screened using the disclosed methods include commercial sources (e.g., commercial peptide libraries), as well as molecules generated using routine methods (e.g., antibodies, RNAi molecules). For example, peptide-based diagnostic specific binding molecules that are not necessarily immunoglobulin in origin can be made using methods that are similar to phage display methods. One such method is described in Szardenings, *J. Recept. Signal Transduct. Res.,* 23:307-309, 2003.

Libraries (such as combinatorial chemical libraries) useful in the disclosed methods include, but are not limited to, peptide libraries (see, e.g., U.S. Pat. No. 5,010,175; Furka, *Int. J. Pept. Prot. Res.,* 37:487-493, 1991; Houghton et al., *Nature,* 354:84-88, 1991; PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA,* 90:6909-6913, 1993), vinylogous polypeptides (Hagihara et al., *J. Am. Chem. Soc.,* 114:6568, 1992), nonpeptidal peptidomimetics with glucose scaffolding (Hirschmann et al., *J. Am. Chem. Soc.,* 114:9217-9218, 1992), analogous organic syntheses of small compound libraries (Chen et al., *J. Am. Chem. Soc.,* 116:2661, 1994), oligocarbamates (Cho et al., *Science,* 261: 1303, 1003), and/or peptidyl phosphonates (Campbell et al., *J. Org. Chem.,* 59:658, 1994), nucleic acid libraries (see Sambrook et al. *Molecular Cloning, A Laboratory Manual,* Cold Springs Harbor Press, N.Y., 1989; Ausubel et al., *Current Protocols in Molecular Biology,* Green Publishing Associates and Wiley Interscience, N.Y., 1989), peptide nucleic acid libraries (see, e.g., U.S. Pat. No. 5,539,083), antibody libraries (see, e.g., Vaughn et al., *Nat. Biotechnol.,* 14:309-314, 1996; PCT App. No. PCT/US96/10287), carbohydrate libraries (see, e.g., Liang et al., *Science,* 274:1520-1522, 1996; U.S. Pat. No. 5,593,853), small organic molecule libraries (see, e.g., benzodiazepines, Baum, C&EN, Jan. 18, page 33, 1993, U.S. Pat. No. 5,288,514; isoprenoids, U.S. Pat. No. 5,569, 588; thiazolidionones and methathiazones, U.S. Pat. No. 5,549,974; pyrrolidines, U.S. Pat. Nos. 5,525,735 and 5,519, 134; morpholino compounds, U.S. Pat. No. 5,506,337) and the like. Additionally, a library of chemical compounds can be obtained, for example from Millennium Pharmaceuticals, Inc. or Celgene Corporation.

Libraries useful for the disclosed screening methods can be produced in a variety of manners including, but not limited to, spatially arrayed multipin peptide synthesis (Geysen, et al., *Proc. Natl. Acad. Sci.,* 81(13):3998-4002, 1984), "tea bag" peptide synthesis (Houghten, *Proc. Natl. Acad. Sci.,* 82(15): 5131-5135, 1985), phage display (Scott and Smith, *Science,* 249:386-390, 1990), spot or disc synthesis (Dittrich et al., *Bioorg. Med. Chem. Lett.,* 8(17):2351-2356, 1998), or split and mix solid phase synthesis on beads (Furka et al., *Int. J. Pept. Protein Res.,* 37(6):487-493, 1991; Lam et al., *Chem. Rev.,* 97(2):411-448, 1997). Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

The compounds identified using the methods disclosed herein can serve as conventional "lead compounds" or can themselves be used as potential or actual therapeutics. In some instances, pools of candidate compounds may be identified and further screened to determine which individual or subpools of compounds in the collective have a desired activity.

The test compound may be administered to a subject (such as an α1G−/−, α1G+/−, or wild type mouse) by any route. In particular examples, the compound is administered parenterally (such as intraperitoneally, intravenously, intramuscularly, subcutaneously, or intradermally), transdermally, or orally. In some examples, the test compound is administered to the subject over a range of dosages (for example, about 1 ng/kg to about 100 mg/kg, such as about 10 ng/kg to about 10 mg/kg, about 100 ng/kg to about 10 mg/kg, about 1 μg/kg to about 10 mg/kg, about 10 μg/kg to about 10 mg/kg, about 100 μg/kg to about 10 mg/kg, or about 10 μg/kg to about 1 mg/kg). Appropriate routes and dosages of administration can be determined by one of skill in the art.

The present invention also provides a method for using an α1G T-type calcium channel inhibitor or an activator as a therapeutic agent for the treatment of novelty-seeking character, alcoholism and stress related diseases.

The above results suggest that α1G gene of α1G T-type calcium channel plays an important role in novelty-seeking character formation, which means an α1G T-type calcium channel inhibitor or an activator can be effectively used for the treatment of nervous diseases such as novelty-seeking character, alcoholism and stress related diseases.

Precisely, fear for a new surrounding, deficiency of the spirit of adventure or stress related diseases are alleviated by inhibiting α1G channel. On the contrary, a character excessively seeking pleasant feeling, which might be a reason for toxic symptoms, is inhibited by activating α1G channel.

The present invention further provides a method for screening medicines for the treatment of novelty-seeking character, alcoholism and stress using a transgenic mouse deficient in α1G T-type calcium channel.

As explained hereinbefore, α1G gene plays an important role in novelty-seeking character formation, making the gene as a useful target subject for screening medicines or developing a treatment method for novelty-seeking character, alcoholism and stress related diseases. Therefore, α1G T-type calcium channel transgenic mice deficient in α1G gene particularly can be effectively used for screening medicines for the treatment of the above diseases.

BRIEF DESCRIPTION OF THE DRAWINGS

The application of the preferred embodiments of the present invention is best understood with reference to the accompanying drawings, wherein.

EXAMPLES

Figure 1:
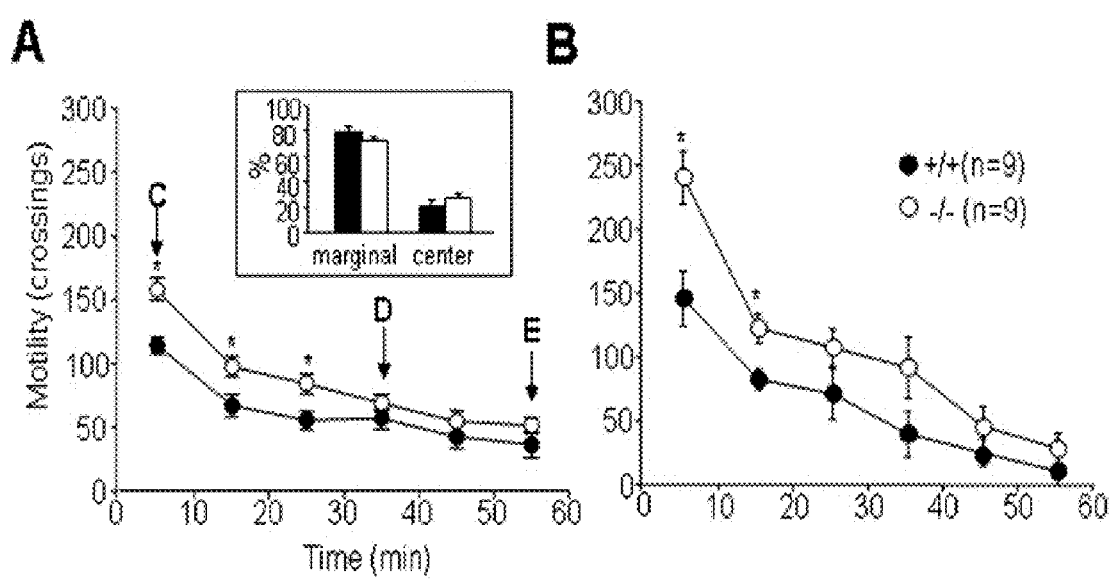
FIG. 1A is a graph showing reactivity of α1G T-type calcium channel transgenic mice to a new environment in an open field.
FIG. 1B is a graph showing reactivity of α1G T-type calcium channel transgenic mice to a new environment in a new breeding cage.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Generation of Transgenic Mice Deficient in α1G T-Type Calcium Channel (α1G−/−)

<1-1> Construction of a Targeting Vector

In order to prepare transgenic mice deficient in a part or some parts of α1G gene of T-type calcium channel, the present inventors referred to the report "TRANSGENIC MOUSE WITH DISRUPTED CALCIUM ION CHANNEL ALPHA 1D GENE AND PRODUCTION METHOD THEREOF" (Korea Application No: 10-2001-0028803) applied for a patent by the present inventors on May 25, 2001.

Particularly, a mouse cDNA of the α1G gene (cacna1G) sequence corresponding to 688-1008 bp of the rat cDNA was isolated by RT-PCR. Using the above isolated sequence as a probe, a bacteriophage lambda FIX II library (Stratagene) wherein DNA fragments of 129/svJae mouse genome were inserted randomly was screened. From this, the genomic phage clone containing α1G gene was selected and confirmed by restriction mapping, Southern blotting, and sequencing.

The targeting vector was designed to delete most of the exon encoding amino acid residues 82-118 that comprise the N-terminus of the α1G protein. To enhance targeting efficiency, a thymidine kinase gene cassette and a negative selection marker were inserted into the 3' of the targeting vector.

<1-2> Culture of Embryonic Stem Cell

A J1 embryonic stem cell line was used for the transfection of the targeting vector constructed in Example <1-1>. J1 embryonic stem cells (obtained from Dr. R. Jaenisch of the Massachusetts Institute of Technology) were maintained in ES medium (DMEM (Gibco Co.) supplemented with 15% fetal bovine serum (Hyclone Co.), 1× penicillin-streptomycin (Gibco Co.), 1× non-essential amino acid (Gibco Co.) and 0.1 mM 2-mercaptoethanol) for two to three days at 37° C. Single cells were obtained by treating the cells with 1 mM EDTA solution containing 0.25% trypsin.

<1-3> Transfection of Targeting Vector

The targeting vector generated in Example <1-1> was introduced by electroporation into the single cells obtained in Example <1-2>. Particularly, 25 μg of targeting vector DNA was added into embryonic stem (ES) cells ($2 \times 10^7$ cells/ml). After mixing, electroporation was performed with 270 V/500 μF. The cells were cultured in an ES medium containing 0.3 mg/ml of G418 and 2 μM of ganciclovir for five to seven days. ES cell clones correctly targeted were selected by using homologous recombination method, and maintained.

<1-4> Generation of Chimera Mice

In order to generate chimera mice having α1G+/− genotype, embryonic stem cell clones selected in Example <1-3> were microinjected into fertilized blastula of C57BL/6J mice.

Particularly, female and male C57BL/6J mice (Jackson Laboratory, USA) were mated, and 3.5 days (3.5 p.c.) after mating, the female mouse was sacrificed by cervical dislocation. Uterus was removed from the sacrificed female mouse and terminal region of the uterus was cut with scissors. Using 1 ml syringe, 1 ml of injection solution containing 20 mM HEPES, 10% FBS, 0.1 mM 2-mercaptoethanol and DMEM was circulated. Blastula was separated from the above uterus using microglasstube under the dissecting microscopy. The separated blastula was transferred into the drop of injection solution placed on 35 mm Petrie dish.

In order to insert the embryonic stem cell clones selected in the above Example <1-3> into the blastula, adjusted inner cell mass direction of blastula to negative pressure with holding pipette using microinjector (Zeiss Co.), and then inserted syringe containing 10-15 embryonic stem cell clones into blastocoel of the blastula, after which changed the pressure into positive pressure, resulting in the insertion of embryonic stem cell clones into blastocoel of the blastula. After mating a female mouse having embryonic stem cell-inserted blastula with a male mouse having undergone vasectomy, transplantation was performed into a uterus of a 2.5 p.c. surrogate mother mouse to induce the development of chimera mice, a kind of hybrids generated from embryonic stem cell clones (J1) and blastula of C57BL/6J mice. For the transplantation, anesthetized the surrogate mother with Avertin (1 mg/kg body weight) and excised the abdomen about 1 cm. Pulled the upper part of uterus out about 2 cm using a pincette, and then made a hole in the uterus with a needle. Inserted the blastula through the hole using a micro glass tube. Took two stitches in the peritoneal membrane with a suture, and then sutured the outer skin with a clip for internal medicine. Transplanted the blastula, in which embryonic stem cells were inserted by the above procedure, into the uterus of the surrogate mother mouse and raised for about 19 days, by which obtained chimera mice having α1G+/− genotype, which resulted from fusion of embryonic stem cell originated cells with blastula originated cells.

<1-5> Generation of α1G+/− Heterozygote Mice

Chimera mice generated in the above Example <1-4> were interbred respectively with C57BL/6J and with 129sv mice more than 6 times, resulting in the preparation of C57BL/6J-α1G+/− and 129sv-α1G+/−. The prepared mice (C57BL/6J-α1G+/− and 129sv-α1G+/−) were mated each other, resulting in α1G+/+ and α1G−/− mice in F1 stage. Those were used for the behavior tests. Mice were raised in a SPF (specific pathogen free) facility with 12 hour-light cycle. PCR was performed to test genotype.

Example 2

Investigation of Behavioral Changes of Transgenic Mice Deficient in α1G T-Type Calcium Channel <2-1> Investigation of Reactivity to a New Environment In order to investigate reactivity to a new environment and a strange subject of α1G calcium channel transgenic mice, the present inventors transferred them to a breeding cage and an open field to observe their behavioral changes.

First, for the analysis of behavioral aspect of a transgenic mouse in a new breeding cage, each mouse was raised dependently in a cage for 24 hours. Then, the mouse was transferred to a new cage and its behavior was recorded for 1 hour by DDC camera. A person who was not informed about its genotype observed the behavior by the recorded tape.

For reactivity test in an open field, a test animal was transferred to a test room one hour before the test began and each animal was put in an independent breeding cage for adaptation. The floor of the open field (white acryl, 50×50×50 cm) was covered with 0.5 cm litter, on which a test animal was put and locomotion of the animal was observed for 1 hour.

Figure 2:
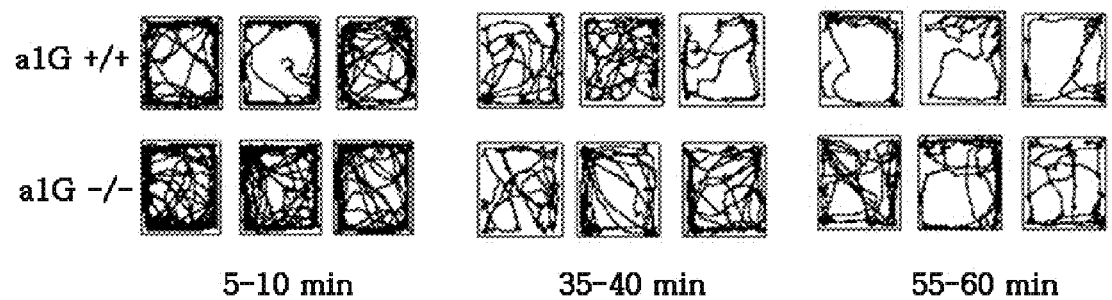
FIG. 2 presents the results of investigation of moving routes of a new subject according to time in each section as a part of reactivity test in the open field.

As a result, mobility of both a wild type α1G+/+ mouse and a transgenic α1G−/− mouse was significantly increased in an early stage while they were searching a new environment. In particular, reactivity to a new subject of a transgenic mouse was much increased, comparing to a wild type (FIGS. 1 and 2). Particularly, when a mouse was freed in an open field, searching motility was increased for the initial 30 minutes, and when an animal was put in a new breeding cage, searching motility was increased for the early 20 minutes. However, the searching motility was no more increased after habituation in both a wild type α1G+/+ mouse and a transgenic α1G−/− mouse, and no difference between the two groups was observed at last.

<2-2> Investigation of Reactivity to a New Subject

In order to verify the result obtained in the above Example <1-1>, the present inventors provided a new material in each cage to investigate reactivity. A mouse was transferred from a familiar old cage to a temporary cage to provide a new material in the old cage. Precisely, two identical subjects (size: 3×3×3 cm, weight: 2.5 g, styrofoam rolled up with paper tape) were put at 10 cm distance from the end of one side. Then, a mouse was back to the familiar cage with its head facing opposite side from the subjects. Its behavior was observed for 15 minutes. The subjects were not fixed on the floor, suggesting they were movable. All the behavior of the test animal during the test was recorded by a video camera for further analysis.

Behavioral analysis was performed by measuring the moving distance for 1 hour; a latency period until the first contact to a new subject; contact time for 15 minutes; contact frequency and pattern; and moving distance of the subject.

"Contact" means when a nose of a mouse was heading toward a new subject within a 2 cm-radius or directly touching the subject. Contact patterns are classified into approaching which means a nose of the test animal is heading toward or directly touching a provided subject, digging which means the animal is digging litters around the subject with its nose heading toward the subject, pushing which means the animal moves the subject with its nose, towing which means the animal moves the subject with its forefeet and biting which means the animal moves the subject with its mouth.

Figure 3:
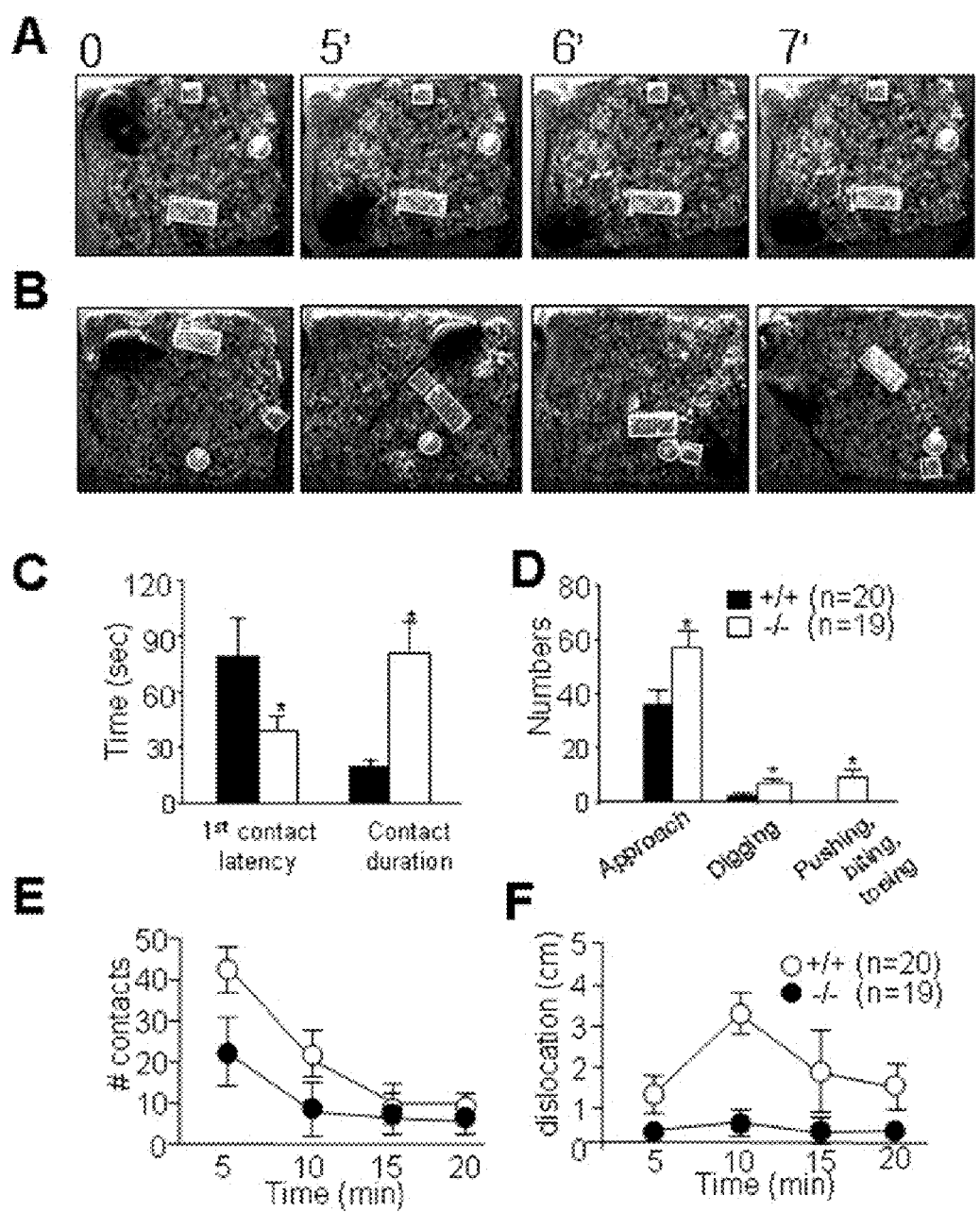
FIG. 3A is a set of photographs showing reactivity of a control (wild type mice) to a new subject, in which moving routes of the subject according to time is seen.
FIG. 3B is a set of photographs showing reactivity of transgenic mice of the present invention to a new subject, in which moving routes of the subject according to time is seen.
FIG. 3C is a graph showing delayed approaching time and contact time to a new subject of both a wild type mouse (α1G+/+) and a transgenic mouse of the present invention (α1G−/−).
FIG. 3D is a graph showing difference in searching behavior for a new subject between a wild type mouse and a transgenic mouse.
FIG. 3E is a graph showing subject contact according to time.
FIG. 3F is a graph showing the results of measurement of moving distance of a subject.

After observing reactivity to a new subject, a unique behavior that has not been observed in any other so far was seen in an α1G−/− mouse. Approaching time to a new material was shorter but contact time was longer, comparing to a wild type mouse (FIG. 3C). Behavioral pattern was also unique, that is, digging around the material, biting, pulling and dragging the material, which were all hardly seen in wild type mice (FIG. 3D). In early stage, a test animal was simply hunting the new circumstance without moving a provided strange material. Upon investigating the new environment, the animal showed play behavior with moving the material (FIGS. 3E and 3F).

<2-3> Analysis of Distinction Capacity

Distinction capacity of the transgenic mice was tested to confirm whether or not unique behavior patterns of α1G−/− mice resulted from visual capacity to recognize a new subject. Particularly, a mouse was trained for three days in an open cage (40×40×40 cm). During the training, two subjects were put in the cage for 5 minutes to be recognized by the mouse. When the mouse was heading its head toward the subject within one-inch distance, the mouse was judged to recognize the subject. After one hour or 24-hour retention, two subjects were put on the same place in the cage but one of them was replaced with a new one, which were left there for 5 minutes to give a mouse chance to recognize them. Time to recognize one of the two subjects or a new one was measured, which would be a good reference for analysis of cognitive memory.

Figure 4:
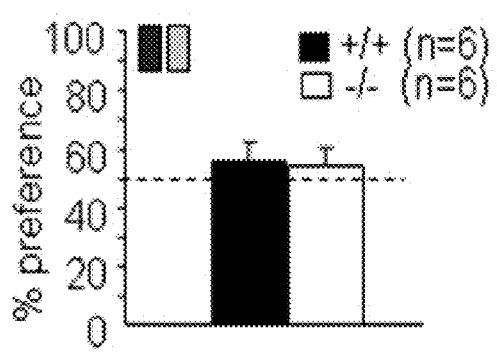
FIG. 4A is a graph showing the results of recognition test, in which the aspects of recognizing two different subjects, which were difficult to be distinguished, of both a wild type mouse (α1G+/+) and a transgenic mouse of the present invention (α1G−/−) were compared.
FIG. 4B is a graph showing the results of the recognition test, in which the aspects of recognizing two different subjects, which were easy to be distinguished, of both a wild type mouse and a transgenic mouse were compared.
Figure 4:
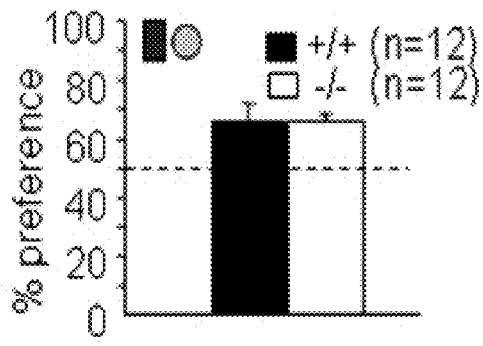

As a result, there was not much difference between α1G−/− mice and wild type mice in visual capacity to recognize a new subject (FIG. 4). The result indicates that difference between α1G−/− mice and wild type mice in behavioral patterns is not because of difference in sensing a new material with eye but because of difference in response (reactivity) of brain.

<2-4> Investigation of Learning Capacity

In order to investigate relation between mobility increase of α1G−/− transgenic mice and diseases showing similar mobility increase, for example, attention-deficit hyperactive disorder, schizophrenia, stereotype, etc, the present inventors performed various tests to measure learning capacity such as rotarod test, Morris water maze test, Fear conditioning, etc.

<2-4-1> Rotarod Test

The rotarod apparatus was used in accelerating mode, gradually increasing from 3 to 35 rpm over the course of 5 minutes. Mice were placed on the apparatus, and rotation was initiated. Latency to fall was recorded for each mouse in a single trial. The mice were trained five times a day with one-hour interval for three days. As a confirmation test, rotarod test was performed 30 days later, 5 times, and time to fall was measured again.

<2-4-2> Fear Conditioning Analysis

Animals learn fear by a new environment or a conditional stimulus (CS) like mild shock on food, especially when it paired with a hateful un-conditional stimulus (US). They show conditional immobility response that is characterized by immobility and shrink right after getting a conditional stimulus. In rodents, lesion of hippocampus is limited to two forms of fear condition: one is non-specific cue (chamber contextual) that is sensitive to the lesion of hippocampus and the other is specific cue (situation) that is not sensitive to the lesion of hippocampus. Contextual condition depends on hippocampus, but cued condition depends on tonsil of cerebellum.

The present inventors used fear regulating shock chamber (19×20×33 cm) containing stainless steel grid (5 mm in diameter, 1 cm away from the bottom), and active monitor (Win-Linc Behavioral Experimental control software, Coulbourn Instruments). In order to give contextual and cued fear, put mice (8-12 weeks old) in fear-conditioned chamber for 2 minutes, during which gave auditory conditional stimulus (CS, white noise) for 20 seconds. For the last 2 seconds, applied 0.5 mA shock as un-conditional stimulus to floor grid. Performed the protocol once. Based on the pilot experiment, determined the intensity of stimulus and the frequency of training to get optimum effect of learning. In order to investigate suggested learning capacity, put animals to new surroundings (new chamber, smell, floor and visual hint) after training and left for 24 hours. Exposed the animals to tone for the last 3 minutes of the test. Investigated fear response by measuring the length of immobility response time with a stopwatch. Observed basal behavior in the new surroundings for 6 minutes and then gave sound CS for 1 minute. Measured both contextual and cued conditions in shock chamber during 24 hours after one time CS/US training.

<2-4-3> Morris Water Maze Test

The water maze apparatus was constituted of round pool (white plastic, 120 cm in diameter, 93 cm in height) containing 24-26° C. water and made opaque with non-toxic water soluble paint. The pool was set in the center of a room (2.5× 2.5 m) and 4 cues were hung on each side of wall. Trained group 1 to find a hidden platform (a circle 10 cm in diameter, located 1 cm beneath water) during 7 sessions (4 times trial/session/day), so did group 2 during 4 sessions. Let mice watch the wall at random. Made mice find the platform for 60 seconds and rest for 30 seconds. When mice could not find the platform within 60 seconds, stopped the mice and let them on the platform for 30 seconds. Carried out transmission test 3 times. The first transmission test was performed with group 1 and 2 at the end of the third session, the second transmission test was performed with group 1 at the end of the second session and the third transmission test was performed with group 2 two weeks after the forth session. While performing transmission test, removed the platform and let the mice swim in the pool for 60 seconds. Followed the traces of the mice with infrared-sensitive camera (Advanced VP 2000) connected to tracker unit. Saved the traces, which were collected by software (HVS Water for windows software, HVS IMAGE Ltd). Analyzed the required time in quadrant and crossing-times of platform.

Used other mice (group 3) for visual platform test and performed hidden platform test using the same water maze. But this time, there were two differences: 3 trials/session/day; black platform, which was moved each time.

Figure 5:
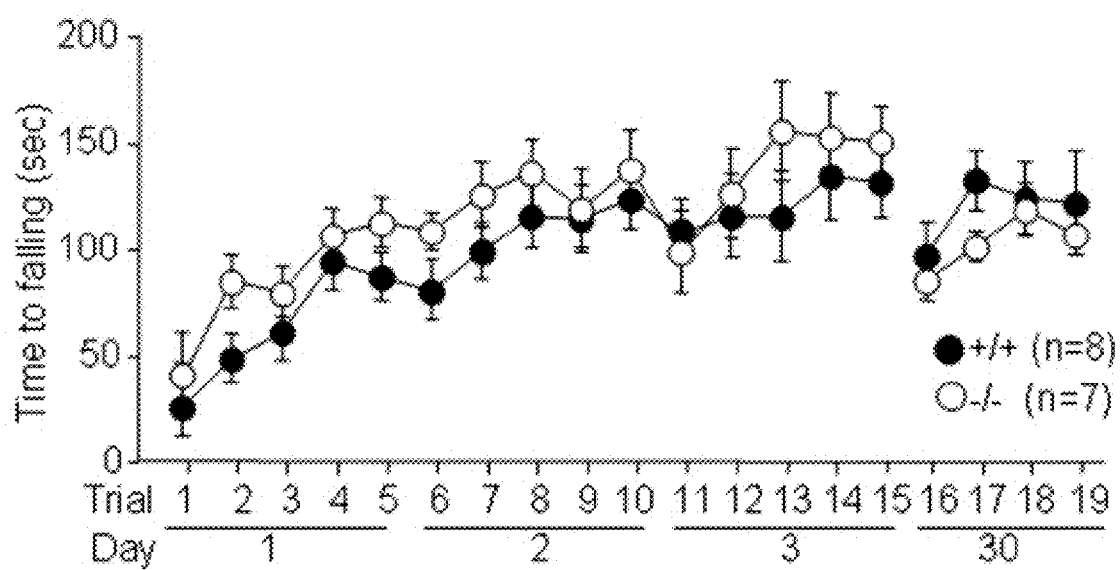
FIG. 5 is a graph showing the results of movement learning test using rotarod apparatus.
Figure 6:
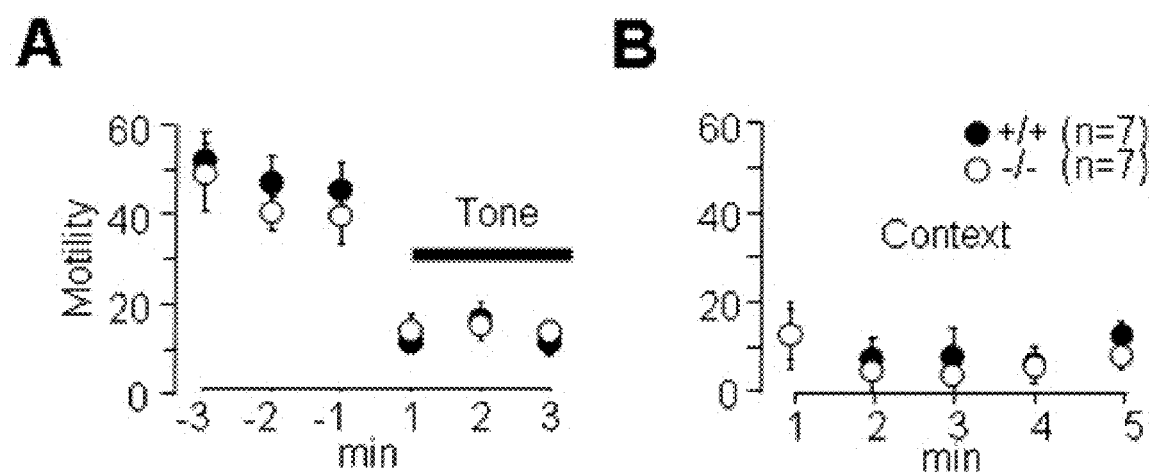
FIG. 6A is a graph showing the decrease of movement against US (tone) stimulus after 24 hour of learning of fear conditioned reflex.
FIG. 6B is a graph showing the decrease of movement affected by space condition after 24 hour of learning of fear conditioned reflex.
Figure 7:
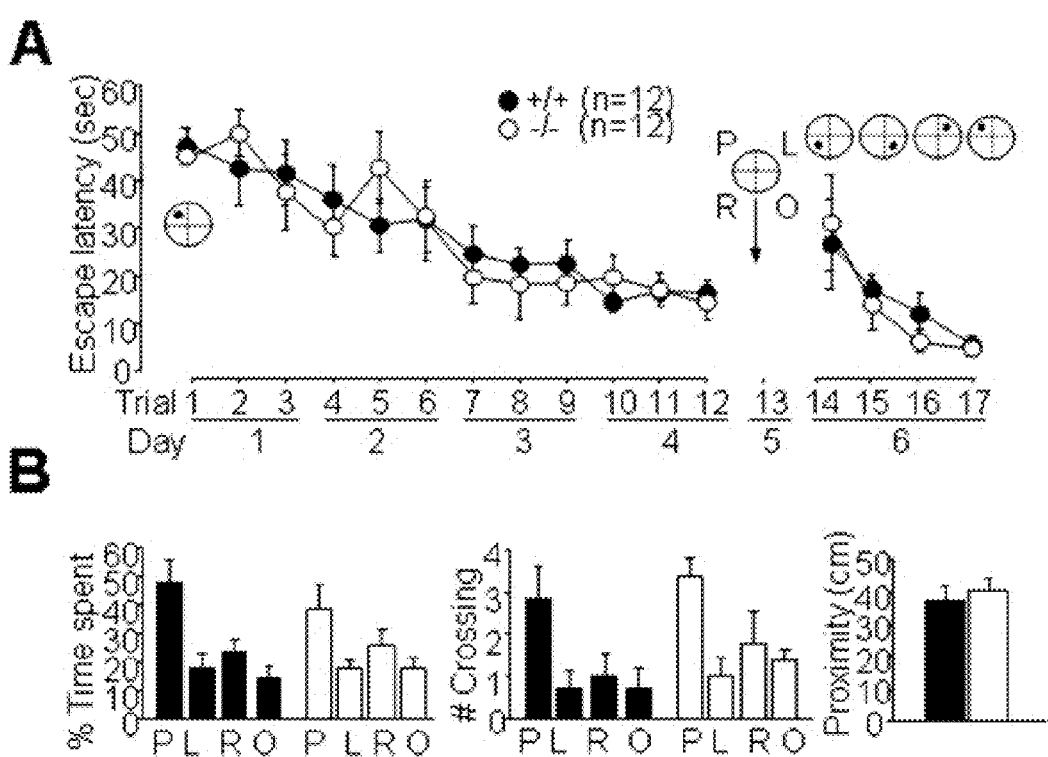
FIG. 7A is a graph showing the results of Morris water maze test.
FIG. 7B is a set of graphs showing the results of Morris water maze test. Precisely, the test was repeated 12 times for 4 days. On day 5, a mouse was put in a water maze without a platform and time spend in quadrant (P) where a platform had been, crossing and proximity were measured.

After testing ability to learn with the above three methods, it was confirmed that there was no difference between transgenic mice and wild type mice in the ability, as shown in FIGS. 5, 6 and 7. Mobility increase exceeding ability to learn, as shown in α1G−/− mice, indicates that mice have a problem of adaptation to a new environment because of short ability to learn. Thus, a new environmental or a new material dependent mobility increase of α1G−/− transgenic mice is a new phenomenon not reported before.

<2-5> Pharmacological Analysis

In order to investigate whether or not mobility increase of α1G−/− transgenic mice is related to diseases such as attention-deficit hyperactive disorder, schizophrenia, stereotype, etc., the present inventors have performed analysis of pharmacological effect of lithium and amphetamine which have been used as a therapeutic agent for the above diseases.

First, the effect of lithium and amphetamine on reactivity to a new subject was investigated. Particularly, one hour before exposing a test animal on an experimental device, lithium or amphetamine (0.5 mg/kg, injection 10 ml/kg) was injected into abdominal cavity of the animal. The test procedure was in accordance with that of reactivity test in an open field, but a breeding cage (24×18×13 cm) took the place of a white acryl open field in this example and a subject used was a styrofoam covered with 0.5 g aluminum foil and the size of which was 1.5×1.5×1.5 cm. Behavior of the animal was all recorded by a video camera for further analysis. Same standard and behavior index were used.

Figure 8:
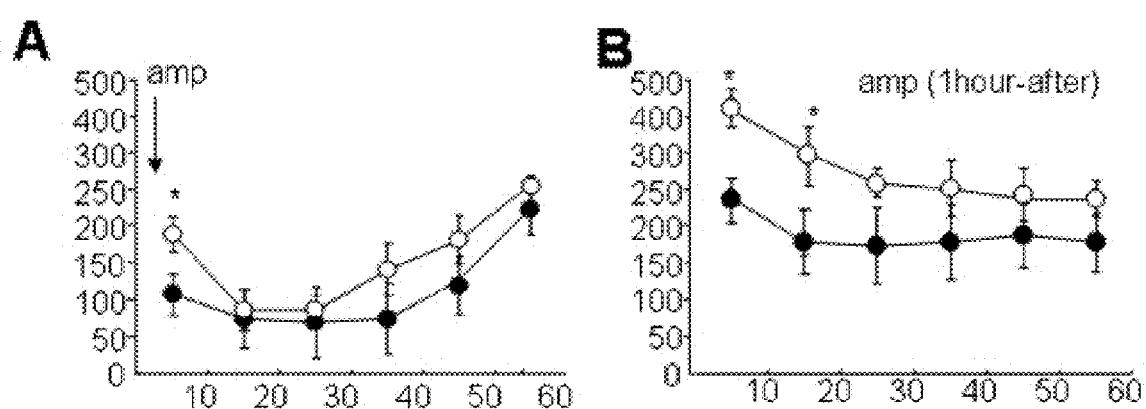
FIG. 8A is a graph showing the changes of mobility upon being left in an open field immediately after amphetamine treatment.
FIG. 8B is a graph showing the changes of mobility upon being left in an open field one hour after amphetamine treatment.

As a result, although amphetamine which has been widely used for the treatment of attention-deficit hyperactive disorder has been known to increase mobility in general but mitigate the mobility increase in a patient with attention-deficit hyperactive disorder Cirulli, F. and Laviola, G., Neurosci Biobehav Rev 24, 73-84, 2000), the early mobility increase of α1G-/- transgenic mice was not mitigated by amphetamine and rather non environment dependent mobility increase was over-induced (FIG. 8).

Figure 9:
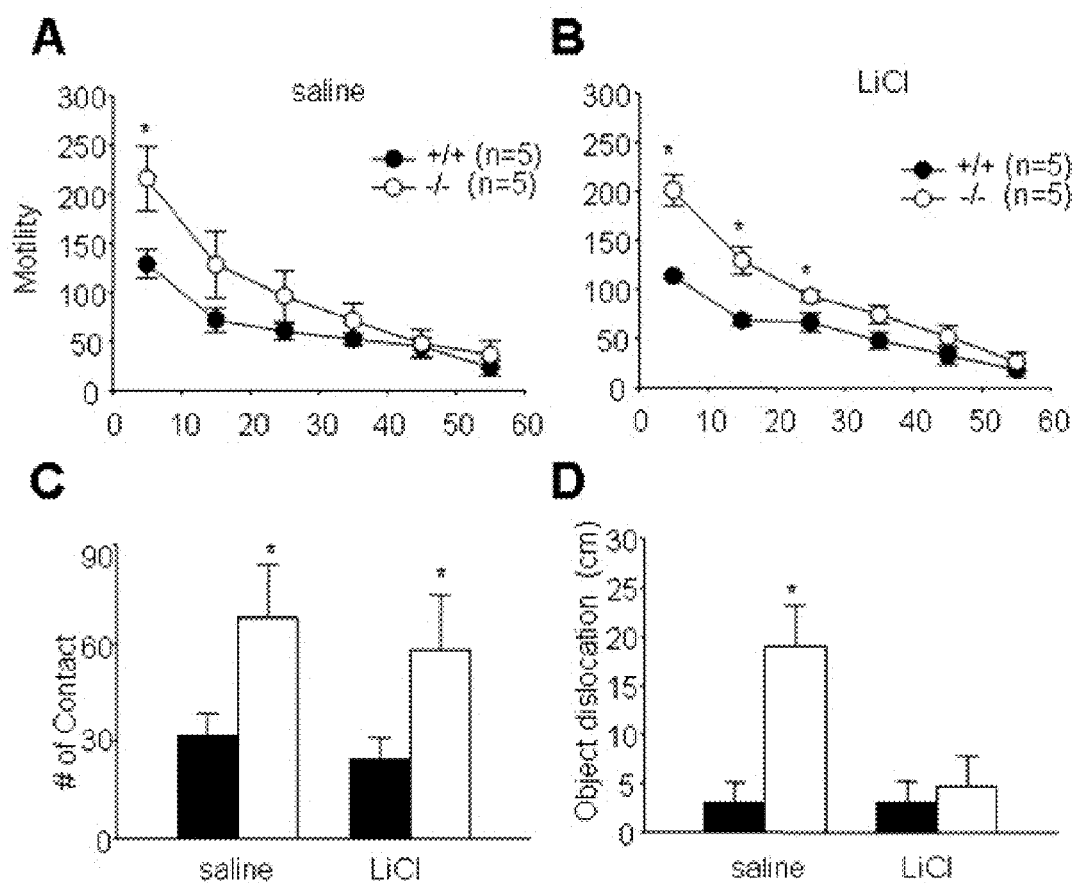
FIG. 9A is a graph showing the changes of mobility in an open field one hour after saline treatment.
FIG. 9B is a graph showing the changes of mobility in an open field one hour after lithium treatment.
FIG. 9C is a graph showing contact frequency to a new subject one hour after saline and lithium treatment.
FIG. 9D is a graph showing moving distance of a new subject one hour after saline and lithium treatment.

The effect of lithium (Nolen, W. A., Ned Tijdschr Geneeskd 143, 1299-1305, 1999), an excitement inhibitor that has been used for the treatment of manic-depression, on mobility was not significant, either. Just reactivity to a new subject of α1G-/- transgenic mice pretreated with lithium was affected a little, so that play behavior was suppressed (FIG. 9) but searching motility was not changed. Therefore, after the pharmacological analysis, the reason of mobility increase of α1G-/- transgenic mice was still unclear. The excessive play behavior with a new subject seen in transgenic mice was believed to be related to emotional changes by brain.

<2-6> Stress Analysis

Figure 10:
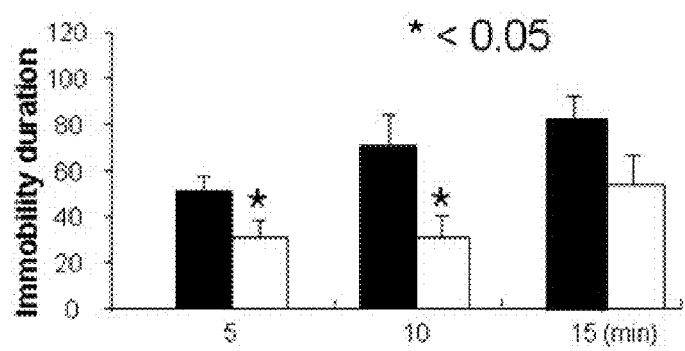
FIG. 10A is a graph showing the results of tail suspension test for the measurement of desperate behavior.
FIG. 10B is a graph showing the results of forced swimming test for the measurement of desperate behavior.
Figure 10:
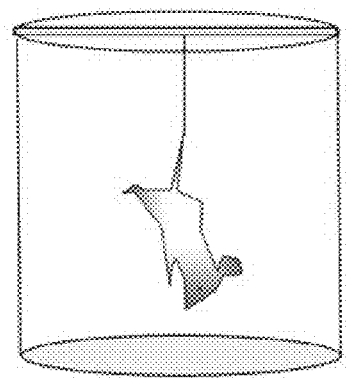
Figure 10:
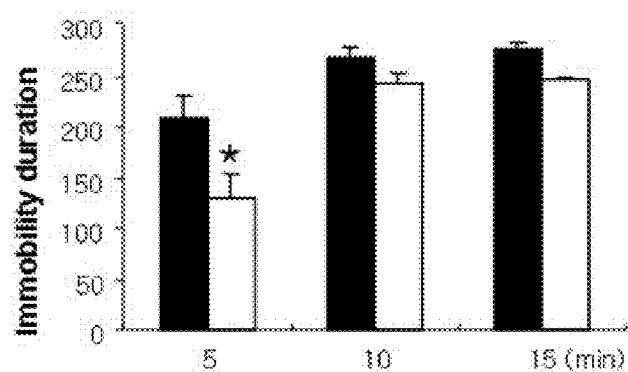
Figure 10:
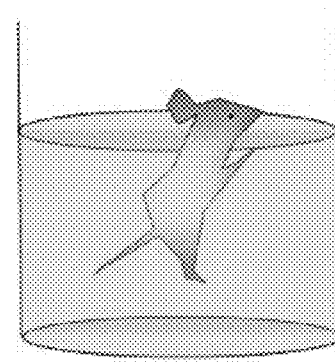

According to previous reports that a man of novelty-seeking character prefers a new environment or stimuli to enjoy excessive or dangerous play behavior and is sensitive to drugs but feels less fear or stress by a new environment or a strange subject, the present inventors investigated whether of not the transgenic mice of the invention had similar characters by forced swimming test and tail suspension test. In those tests, time of immobility that mice gave up escaping because of over-stress and depression was increased. Anti-depressants have been known to shorten the immobility time. As a result, immobility time of α1G-/- transgenic mice was shortened (FIG. 10). So, like people having novelty-seeking character, α1G-/- transgenic mice are less sensitive to a new environment causing stress or depression.

<2-7> Investigation of Alcohol Preference by Two-Bottle Choice Test

Two different bottles of water were provided to the test animal to make it be familiar with them. Then, mice of group 1 were provided with one bottle of water and the other bottle of 10% alcohol and the amount they drink was measured for a week from the day one of bottle change. The location of the two bottles was exchanged each other every three days. One of the two water bottles was replaced by a bottle of 0.015 M quinine for group 2 and by a bottle of 0.033% saccharine for group 3. And the amounts of them consumed were compared with that of water drunk.

Figure 11:
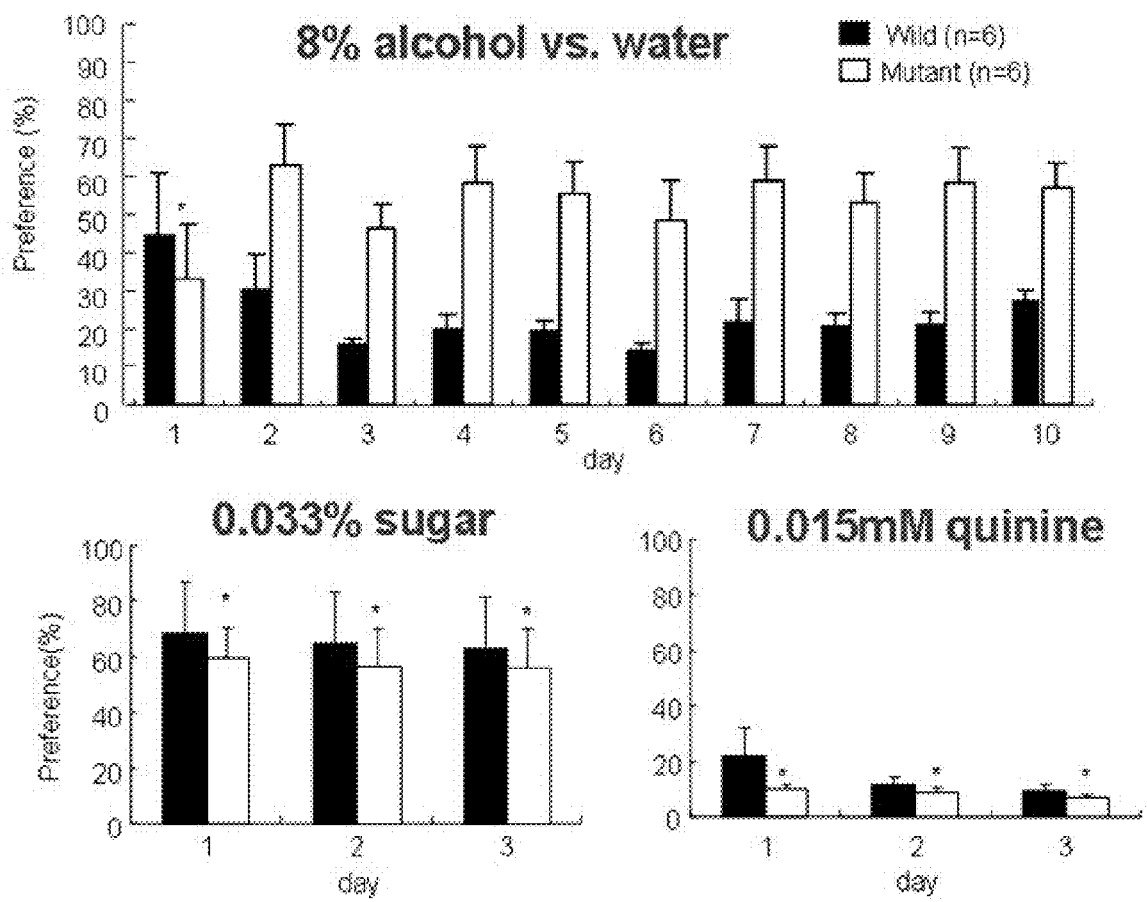
FIG. 11 is a set of graphs showing the results of two-bottle choice test, in which preference was investigated between alcohol and water, between sugar and water, and between quinine and water.

As a result, alcohol preference of α1G-/- transgenic mice was significantly increased, comparing to wild type mice. However, preference of saccharine giving a sweet taste or preference of quinine having a bitter taste was not changed (FIG. 11). These results indicate that sensitivity to flavor is not a reason for alcohol preference.

Example 3

Methods of Screening for Compounds for Inhibiting Novelty Seeking Behavior or Alcoholism The α1G-/- mice described herein are used to identify compounds that could be used to inhibit novelty seeking behavior or for treating alcoholism.

Candidate or test compounds are administered to α1G mice (including wild type, α1G+/-, and/or α1G-/- mice) and the behavior of the mice in tests of novelty seeking behavior (such as reactivity to a new environment or reactivity to a new subject) or alcohol preference are tested. A candidate compound is identified as a compound that inhibits novelty seeking behavior or alcoholism if the compound decreases the behavior of treated mice as compared to untreated mice. In particular, a candidate compound is identified as a compound that inhibits novelty seeking behavior or alcoholism if it decreases the behavior of α1G-/- mice treated with the compound as compared to untreated α1G-/- mice.

The α1G mice are treated with one or more test compounds (dosage ranging from 1 ng/kg to 100 mg/kg). In one example, the test compound is provided by intraperitoneal administration. In other examples, the test compound is provided by oral administration. Behavioral tests are performed immediately and at later time points (such as one hour, two hours, three hours, four hours, six hours, eight hours, twelve hours, or twenty-four hours later), as appropriate for the behavioral test.

Compounds that inhibit novelty seeking behavior are identified using the tests of reactivity to a new environment, such as motility in a new cage or in an open field, as described in Examples 2-1 and 2-5. Compounds that inhibit novelty seeking behavior are also identified using the test of reactivity to a new subject (object or material), as described in Examples 2-2 and 2-5. A compound that inhibits reactivity of a treated α1G-/- mouse to a new environment or a new material by at least 10% as compared to an untreated α1G-/- mouse indicates that the compound is an inhibitor of novelty seeking behavior.

Compounds that inhibit alcoholism are identified using the two bottle alcohol preference test as described in Example 2-7. A compound that inhibits alcohol preference of a treated α1G-/- mouse by at least 10% as compared to an untreated α1G-/- mouse indicates that the compound is an inhibitor of alcohol preference and/or alcoholism.

In conclusion, α1G-/- transgenic mice are very sensitive to but getting less stress from a new environment or a strange subject and drugs, which is very similar character to novelty-seeking character of a man. Thus, the transgenic mice of the present invention can be excellent animal models for the investigation of merits and demerits of such character. And, α1G gene is considered to play an important role in novelty-seeking character forming, so it can be a useful candidate for the development of a new treatment method for nervous diseases and for the screening of a proper medicine.

INDUSTRIAL APPLICABILITY

As explained hereinbefore, the present invention relates to a use of α1G T-type calcium channel transgenic mice showing a novelty-seeking character and alcohol preference as a model for study on human nervous diseases related to emotion and anxiety disorders. Therefore, the animal model provided by the present invention can be effectively used for the development of a medicine and a treatment method for the human nervous diseases including novelty-seeking character, alcoholism and other stress-related diseases.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of identifying a compound with potential for treatment of novelty-seeking character or alcoholism comprising:
   a) administering one or more test compounds to a α1G T-type calcium channel knockout mouse having α1G−/− genotype, wherein the mouse is an animal model of novelty-seeking character or alcoholism; and
   b) determining whether the test compound inhibits at least one behavioral aspect of said mouse related to novelty-seeking character or alcoholism; wherein inhibition of the behavioral aspect is indicative of a compound with potential for treatment of novelty-seeking character or alcoholism.

2. The method according to claim 1, wherein the test compound inhibits the at least one behavioral aspect of said mouse as compared to α1G−/− mice that are not administered the test compound.

3. The method according to claim 1, wherein the behavioral aspect is reactivity to a new environment, reactivity to a new subject, or alcohol preference.

4. The method according to claim 3, wherein the reactivity to a new environment comprises mobility in a new cage or mobility in an open field.

5. The method according to claim 1, wherein the α1G T-type calcium channel knockout mouse shows increased reactivity to a new environment, increased reactivity to a new subject, or increased alcohol preference compared to wild type mice.

6. The method according to claim 1, wherein the test compound comprises a small molecule, an antibody, a peptide, or a siRNA.

7. The method according to claim 6, wherein the test compound comprises lithium.

8. A method of identifying a compound for treatment of novelty-seeking character comprising:
   a) administering one or more test compounds to a α1G T-type calcium channel knockout mouse having α1G−/− genotype, wherein the mouse is an animal model of novelty-seeking character; and
   b) determining whether the test compound inhibits searching action for a new material or play behavior with the new material, wherein inhibition of the searching action or the play behavior is indicative of a compound for treatment of novelty-seeking character.

9. The method according to claim 8, wherein the α1G T-type calcium channel knockout mouse shows increased searching action for a new material or play behavior with the new material compared to wild type mice.

10. The method according to claim 8, wherein the test compound inhibits the searching action or play behavior of said mice as compared to α1G−/− mice that are not administered the test compound.

11. A method of identifying a compound for treating alcoholism comprising:
   a) administering one or more test compounds to a α1G T-type calcium channel knockout mouse having α1G−/− genotype, wherein the mouse is an animal model of alcoholism; and
   b) determining whether the test compound inhibits alcohol preference, wherein inhibition of the alcohol preference is indicative of a compound for treatment of alcoholism.

12. The method according to claim 11, wherein the α1G T-type calcium channel knockout mouse shows increased alcohol preference compared to wild-type mice.

13. The method according to claim 11, wherein the test compound inhibits the alcohol preference of said mouse as compared to α1G−/− mice that are not administered the test compound.

* * * * *